United States Patent [19]

Liebermann

[11] 4,392,374
[45] Jul. 12, 1983

[54] TRANSDUCER COUPLING APPARATUS FOR INHOMOGENEITY DETECTOR

[75] Inventor: Leonard N. Liebermann, La Jolla, Calif.

[73] Assignee: Tif Instruments, Inc., Miami, Fla.

[21] Appl. No.: 271,257

[22] Filed: Jun. 8, 1981

[51] Int. Cl.³ ............................................. G01N 29/02
[52] U.S. Cl. ............................................. 73/19; 73/644
[58] Field of Search ............ 73/19, 61 R, 644, 861.18; 310/323, 328, 334, 336

[56] References Cited

U.S. PATENT DOCUMENTS

| | | | |
|---|---|---|---|
| 2,573,390 | 10/1951 | Blanchard | 73/19 |
| 3,046,780 | 7/1962 | Liebermann | 73/53 |
| 3,974,681 | 8/1976 | Namery | 73/19 |
| 4,014,211 | 3/1977 | Araki et al. | 73/644 |
| 4,015,464 | 4/1977 | Miller et al. | 73/61 R |
| 4,138,879 | 2/1979 | Liebermann | 73/19 |
| 4,235,095 | 11/1980 | Liebermann | 73/19 |

Primary Examiner—Stephen A. Kreitman
Attorney, Agent, or Firm—Pennie & Edmonds

[57] ABSTRACT

A transducer coupling member for use with systems for detecting inhomogeneities in fluids flowing in a conduit. A first portion of the member is acoustically coupled to the conduit wall. An electromechanical transducer is mounted upon another portion. These two portions are partially acoustically coupled. The composite system forms a bandpass filter which eliminates frequencies and modes of oscillation which travel largely in the conduit, thus preventing the system from being rendered insensitive to inhomogeneities. The bandpass automatically adjusts to accommodate a variety of conduits.

6 Claims, 5 Drawing Figures

TRANSDUCER COUPLING APPARATUS FOR INHOMOGENEITY DETECTOR

TECHNICAL FIELD

This invention relates to improvements in devices for detecting inhomogeneities such as gas bubbles in a fluid such as a liquid in a conduit. In particular it relates to an acoustically conductive coupling member for coupling mechanical or acoustic energy from a vibrating electromechanical transducer to the wall of the conduit.

BACKGROUND ART

U.S. Pat. Nos. 4,138,879 and 4,235,095 to Liebermann disclose systems for detecting inhomogeneities in a fluid within a conduit. In these systems a pair of electromechanical transducers are disposed on a fluid-filled conduit in an acoustically coupled relationship. An adjustable-gain driving amplifier responsive to the output of one transducer for driving the other transducer has its gain automatically adjusted to maintain the system on the margin of oscillation. An indicating circuit detects modulation of the driving signal. Inhomogeneities such as bubbles passing through the conduit near the transducers cause variations in the gain required to maintain the system on the margin of oscillation and are detected as modulations of the driving signal.

For many applications of the device disclosed in the above-mentioned patents there are no stringent requirements for the manner in which the acoustic energy is coupled from the transducer to the conduit. This is generally true where the conduit has a very large diameter-to-wall thickness ratio or when only certain modes of oscillation of, for eample, a pipe wall will occur. In such applications the transducers may be coupled to the conduit or pipe by coupling members of simple construction. For example, the transducers may be mounted on thin metal plates which are secured in an apparatus for holding these plates in contact with the conduit wall. Alternatively, the transducers may be glued to a portion of a metal or plastic clamp fastened directly to the outside of the conduit by means such as a spring or thumb screw. Acoustic energy passes directly through the clamp to the conduit wall.

In many applications the detecting apparatus becomes insensitive to bubbles if the transducer mounting means described above is clamped in a slightly different configuration on the same conduit. Random displacement followed by reclamping sometimes restores sensitivity. These insensitive configurations are accompanied by modes of oscillation which are generally much higher, but sometimes lower in frequency than the more sensitive modes. These undesirable oscillations represent vibrational modes of the conduit and coupling member system in which acoustic energy travels primarily in the conduit, rather than in the fluid.

An electrical filter is not a desirable solution to this problem because the coupling member and pipe each contribute to the mode of oscillation. An electrical filter inserted into the system would have a fixed frequency which would not readily accommodate changes in conduit size, clamping configuration and other application parameters.

DISCLOSURE OF THE INVENTION

The present invention solves this problem by providing acoustically conductive coupling members between the transducers and the conduit which become a mechanical bandpass filter that automatically excludes unwanted frequencies of oscillation of the system. The coupling members have a first portion configured with a surface which contacts the conduit over an area sufficient to transmit mechanical energy between the member and the conduit, and a second portion which is spaced apart from the conduit wall upon which a transducer is mounted. These first and second portions are coupled to one another partially so that the first portion and the conduit wall may oscillate in a mode of oscillation distinct from the mode of the combination of the transducer and the second portion. In other words coupling is not so complete that only a single composite mode of oscillation is possible. Each member may further comprise a thin conductive portion for conducting acoustic energy from the first portion to the second portion. The thickness of such conductive portion is preferably equal to or less than that of the thinner of the first and second portions.

In a preferred embodiment the coupling member comprises an extension of a C-shaped body or clamp with a screw for securing the clamp to the conduit. The conductive portion is defined by the dimension of a slot in the coupling member between the first and second portions. The location of a cylindrical bore at the end of the slot may define the thickness of the conducting portion. This bore may be parallel to the conduit and extend through the coupling member.

In an alternate embodiment the first and second portions are substantially planar legs of an L-shaped member. The leg which comprises the first portion is narrower than the leg which comprises the second portion. The connecting members are secured to the conduit by means such as hose clamps.

BRIEF DESCRIPTION OF THE DRAWING

Further objects and advantages of the invention may readily be ascertained by reference to the following descriptions and appended drawings in which.

DETAILED DESCRIPTION OF THE INVENTION

Figure 1:
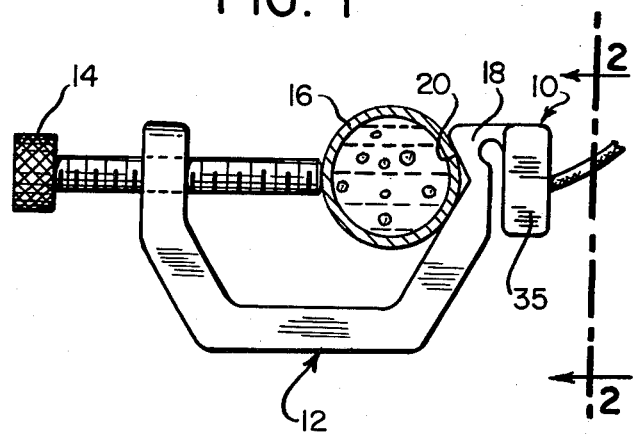
FIG. 1 is a plan view of the apparatus of the invention in the form of an extension of a clamp, showing a conduit of circular cross section.
Figure 2:
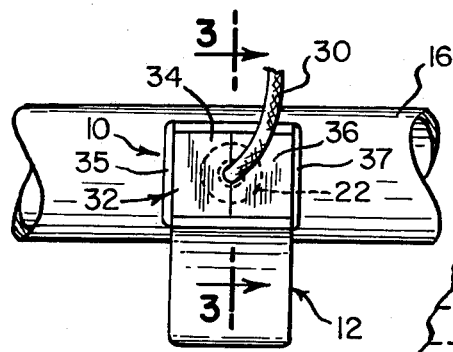
FIG. 2 is taken along line 2—2 of FIG. 1.

Referring to FIGS. 1 and 2 the coupling member 10 of the present invention is shown as an extension of a C-shaped member or clamp 12. Coupling member 10 and clamp 12 are integrally fabricated from extruded aluminum or other convenient metal or acoustically conductive material. The clamp is shown as approximately 1.5 times its normal size. A thumb screw 14, threaded through a distal end of clamp 12, is provided for securing the clamp to conduit 16 which is shown as being of circular cross section. Portion 18 has a surface 20 which is configured to contact conduit 16 tangentially along straight lines parallel to the longitudinal axis of conduit 16. Surface 20 may have a V shape in order to accommodate conduits of drastically different cross sections. Alternatively surface 20 may be contoured to conform to a conduit wall.

Figure 3:
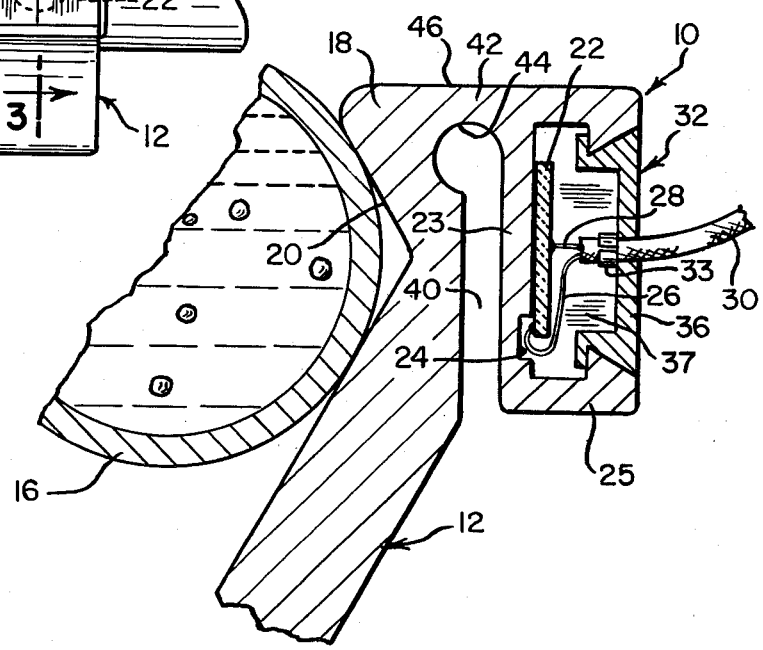
FIG. 3 is an enlarged cross sectional view of a portion of FIG. 1 taken along line 3—3 of FIG. 2.

Referring to FIG. 3, a disc-shaped electromechanical transducer 22 comprised of a barium titanate or lead zirconate titanate of a thickness between 0.010 and 0.020 inches with metallically plated planar surfaces is cemented with a cyanoacrylic material such as Eastman 910 or an epoxy to plate 23 of portion 25 of coupling member 10. Plate 23 has a thickness of approximately 0.065 inches. Portion 25 is apart from (in other words not in mechanical contact with) the wall of conduit 16. A small longitudinal groove or slot 24 conveniently formed during extrusion provides a recess for a solder ball formed when wire 26 is soldered to one of the metallically plated planar surfaces of transducer 22. Wire 28 is soldered to the other plated planar surface. These wires extend from a cable 30 which is anchored to a cap 32 by means of sleeve 33, a split cylinder that is cemented to cable 30. The cap is composed of parts 34 and 36 as may be more readily appreciated with reference to FIG. 2. Parts 34 and 36 have integral extensions or end portions 35 and 37 which form side walls to close off the otherwise open ends of portion 25. A cement is applied to the surfaces of parts 34 and 36 which contact portion 25 and the surfaces of parts 34 and 36 which contact one another. Parts 34 and 36 are then snapped in place.

Cable 30 is used to electrically connect transducer 22 to an electronic apparatus comprising a means for driving one of a pair of transducers mounted in transducer assemblies and a means for sensing variations in the driving signal supplied to one of them as disclosed in U.S. Pat. Nos. 4,138,879 and 4,235,095 to Liebermann. It is understand that in the system described in these patents two transducer assemblies are used. In the preferred method of using the present invention two clamps 12 with coupling members 10 are disposed on conduit 16, so that acoustic coupling occurs between them.

Although the precise mechanical arrangement of the clamps in conduit 16 is not critical and may be varied somewhat on particular applications, it is required that substantially all of this acoustic coupling occur through conduit 16. There must be no substantial direct acoustic compling between the clamps which results from intimate mechanical contact between them, or the system will be rendered insensitive to inhomogeneities in the fluid.

Slot 40 with a width of approximately 0.094 inches separates portions 18 and 25 of coupling member 10. Its depth determines the thickness of conducting portion 42 which conducts sound from portion 18 to portion 25. The location of cylindrical bore 44 typically of a diameter of 0.125 inches at the end of slot 40 provides a convenient way of defining the thickness of conducting portion 42, which is typically 0.065 inches. The hole siz is not critical but its location with its center typically 0.100 inches from the edge 46 of coupling member 10 determines the bending elasticity of the portion 25, as a vibrating member, with respect to portion 18. The vibrational frequency of portion 25 as determined by the mass and thickness of the metal-transducer combination, the abovementioned elasticity as determined by the location of hole 44, and the conduit itself all determine the frequency of vibration of the composite filter produced as a result of the close coupling of portion 18 to the pipe.

Figure 4:
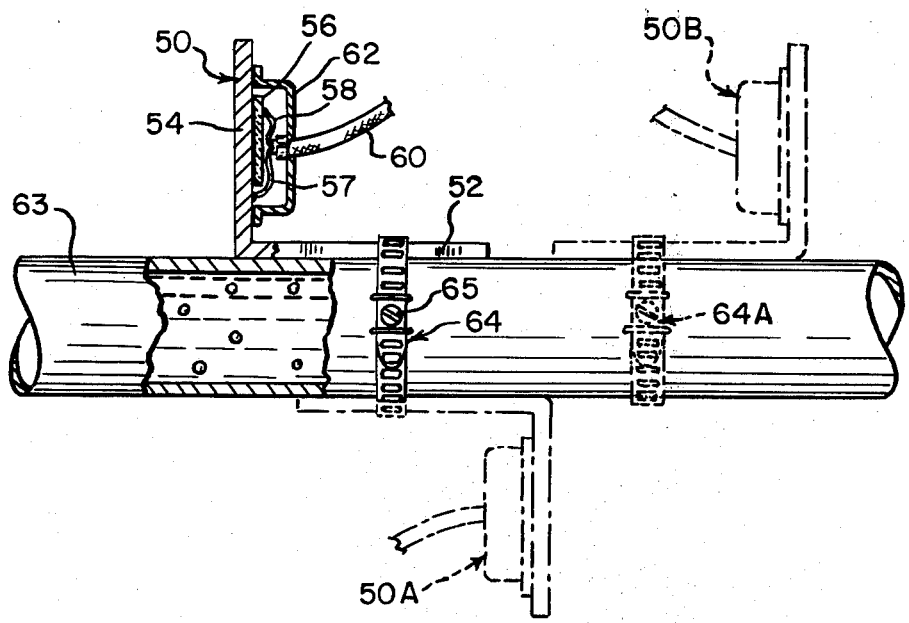
FIG. 4 is a cross sectional side elevation of an alternate embodiment of the invention mounted on a conduit.
Figure 5:
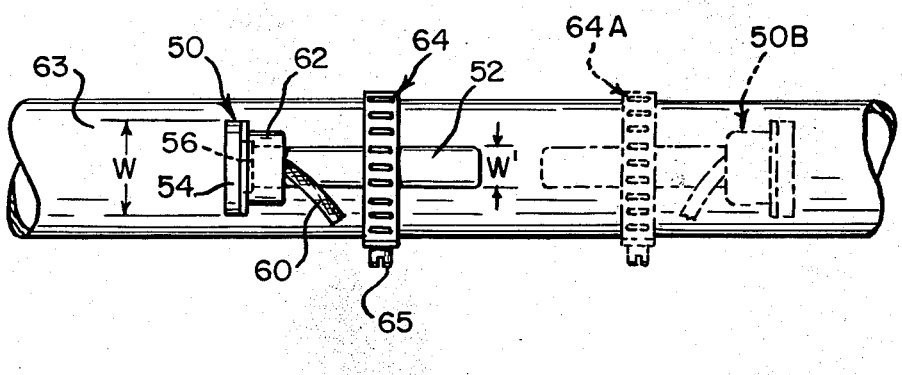
FIG. 5 is a plan view of the apparatus of FIG. 4.

Referring to FIGS. 4 and 5, an alternate embodiment of the invention is shown. It comprises an L-shaped coupling member 50 formed of brass with a thickness of approximately 0.031 inches. The portion or leg 52 which contacts the conduit is narrower than the portion or leg 54 upon which the transducer 56 is mounted so that it may more readily seat on the conduit. In other words the dimension W' is smaller than the dimension W. Each leg is approximately 0.75 inches long. A conductive epoxy may be used to cement transducer 56 to portion 54. Wire 57 which is soldered to portion 54 and wire 58 which is soldered to transducer 56 are connected to cable 60 which is anchored to cover 62. Again the mass and thickness of the transducer metal combination are major parameters governing the frequency or vibration or bandpass of the mechanical filter formed, but the pipe or conduit 63 also exerts an influence.

A metal hose clamp 64 secures coupling member 50 to the pipe. Clamp 64 is tightened around conduit 63 by rotation of screw 65. The pair of coupling members 50 are preferably disposed opposite one another and somewhat axially displaced on the conduit 63 as represented by coupling member 50A in FIG. 4. They may also in some applications be mounted adjacent one another as represented by coupling member 50B. An additional hose clamp 64A must then be used. They should not directly contact one another, however, as direct acoustic coupling between them may result and render the system insensitive to inhomogeneities in the fluid.

It is possible to provide partial acoustic coupling between a portion of a coupling member coupled to a conduit and a portion upon which a transducer mounts by configuring the member as described above. Partial coupling may also be provided by disposing an elastomeric material such as a rubber or a polyurethane betwen noncontacting portions of a coupling member. The elastomer is thus an acoustic conductor of a material and dimension selected to provide a lesser degree of acoustic coupling then that provide by maximum mechanical contact between the first and second portions.

While the invention has been described in connection with only a small number of specific embodiments, it is to be understood that these are merely illustrative of the many other specific embodiments which can also utilize the principles of the invention. Numerous and varied devices can be made by those skilled in the art without departing from the spirit and scope of the present invention, as defined by the following claims.

I claim:

1. In a detector for detecting inhomogeneities in fluid flowing through a conduit including electro-mechanical transducer assemblies disposed on the wall of such conduit in an acoustically coupled relationship with substantially all acoustic coupling occurring through such conduit and means for sensing variations in a driving signal supplied to a transducer on one of said transducer assemblies caused by such inhomogeneities, the improvement comprising:

an acoustically conductive coupling member for coupling a transducer to such conduit; said coupling member including;

a first portion configured with a surface for contacting such conduit wall over an area sufficient to transmit mechanical energy between the member and such conduit wall; and a second portion spaced apart from such conduit wall upon which a transducer is mounted;

said first and second portions being partially acoustically coupled together to form a mechanical filter means for mechanically filtering out undesirable oscillations resulting from vibrational modes of the conduit and coupling member system in which acoustic energy travels primarily in the conduit, rather than in the fluid.

2. In a detector for detecting inhomogeneities in fluid flowing through a conduit including electro-mechanical transducer assemblies disposed on the wall of such conduit in an acoustically coupled relationship with substantially all acoustic coupling occurring through such conduit and means for sensing variations in a driving signal supplied to a transducer on one of said transducer assemblies caused by such inhomogeneities, the improvement comprising:

an acoustically conductive coupling member for coupling a transducer for such conduit; said coupling member including;

a first portion configured with a surface for contacting such conduit wall over an area sufficient to transmit mechanical energy between the member and such conduit wall;

a second portion spaced apart from such conduit wall upon which a transducer is mounted; and means for acoustical contact between the first and second portions comprising an acoustical conductor of a material and dimension selected to provide a lesser degree of acoustic coupling than that provided by maximum mechanical contact between said portions;

wherein said conductive portion is defined by the width of a slot in said coupling member between said first portion and said second portion; and in which the thickness of said conductive portion is defined by the location of a cylindrical bore which terminates said slot.

3. The coupling members as defined in claim 2 in which said cylindrical bore extends generally parallel to said conduit wall.

4. The coupling member as defined in any of claims 2 or 3 configured to form a portion of a C-shaped member comprising a securing screw having an end extending from a distal portion of said C-shaped member toward said surface for contacting such conduit wall whereby said C-shaped member is securable to such conduit by positioning said C-shaped member so that said conduit is between and in intimate mechanical contact with said screw end and said surface, and tightening said screw.

5. In a detector for detecting inhomogeneities in fluid flowing through a conduit including electro-mechanical transducer assemblies disposed on the wall of such conduit in an acoustically coupled relationship with substantially all acoustic coupling occurring through such conduit and means for sensing variations in a driving signal supplied to a transducer on one of said transducer assemblies caused by such inhomogeneities, the improvement comprising:

an acoustically conductive coupling member for coupling a transducer to such conduit; said coupling member including;

a first portion configured with a surface for contacting such conduit wall over an area sufficient to transmit mechanical energy between the member and such conduit wall; and a second portion spaced apart from such conduit wall upon which a transducer is mounted;

said first and second portions being partially acoustically coupled together; wherein said first and second portions comprise substantially planar legs of an L-shaped member; and wherein said leg which comprises said first portion is narrower than said leg which comprises said second portion.

6. In a detector for detecting inhomogeneities in fluid flowing through a conduit including electromechanical transducer assemblies disposed on the wall of such conduit in an acoustically coupled relationship with substantially all acoustic coupling occurring through such conduit and means for sensing variations in a driving signal supplied to a transducer on one of said transducer assemblies caused by such inhomogeneities, the improvement comprising:

an acoustically conductive coupling member for coupling a transducer to such conduit; said coupling member including;

a first portion configured with a surface for contacting such conduit wall over an area sufficient to transmit mechanical energy between the member and such conduit wall;

a second portion spaced apart from such conduit wall upon which a transducer is mounted; said first and second portions being partially acoustically coupled together to form a mechanical filter means for filtering out undesirable oscillations resulting from vibrational modes of the conduit and coupling member system in which acoustic energy travels primarily in the conduit, rather than in the fluid; and a conductive portion providing said partial acoustic coupling, the conductive portion being integral with the first and second portions and defined by the width of a slot in said coupling member generally perpendicular to the conduit and between the first and second portions.

* * * * *

UNITED STATES PATENT AND TRADEMARK OFFICE
CERTIFICATE OF CORRECTION

PATENT NO. : 4,392,374

DATED : July 12, 1983

INVENTOR(S) : Leonard N. Liebermann

It is certified that error appears in the above-identified patent and that said Letters Patent is hereby corrected as shown below:

```
Column 1, line 34, "eample"
should read:
--example--.

Column 3, line 42, "in"
should read:
--on--.

Column 3, line 43, "on"
should read:
--in--.

Column 3, line 58, "siz"
should read:
--size--.

Column 4, line 40, "then"
should read:
--than--.

Column 5, line 18, (Claim 2) "for"
should read:
--to --.
```

Signed and Sealed this

Twenty-seventh Day of September 1983

[SEAL]

Attest:

GERALD J. MOSSINGHOFF

*Attesting Officer*     *Commissioner of Patents and Trademarks*